United States Patent [19]

Cornell et al.

[11] Patent Number: 5,264,609

[45] Date of Patent: Nov. 23, 1993

[54] PREPARATION OF PROPENOIC ACID DERIVATIVES

[75] Inventors: Clive L. Cornell, Saffron Walden; Ian C. Richards, Haverhill, both of England

[73] Assignee: Schering Agrochemicals Limited, England

[21] Appl. No.: 856,896

[22] PCT Filed: Nov. 15, 1990

[86] PCT No.: PCT/GB90/01763

§ 371 Date: May 14, 1992

§ 102(e) Date: May 14, 1992

[87] PCT Pub. No.: WO91/07385

PCT Pub. Date: May 30, 1991

[30] Foreign Application Priority Data

Nov. 18, 1989 [GB] United Kingdom ............... 8926135
Apr. 7, 1990 [GB] United Kingdom ............... 9007938

[51] Int. Cl.$^5$ ............... C07C 69/76; C07C 317/06; C07C 229/28
[52] U.S. Cl. ............... 560/8; 560/9; 560/11; 560/15; 560/37; 560/60
[58] Field of Search ............... 560/8, 9, 15, 60, 11, 560/37

[56] References Cited

FOREIGN PATENT DOCUMENTS

| 0256667 | 7/1987 | European Pat. Off. |
|---------|--------|---------------------|
| 0260794 | 3/1988 | European Pat. Off. |
| 0278595 | 8/1988 | European Pat. Off. |
| 0336211 | 3/1989 | European Pat. Off. |
| 2202843 | 10/1988 | United Kingdom |
| 2218702 | 11/1989 | United Kingdom |

Primary Examiner—Paul J. Killos
Assistant Examiner—Joseph M. Conrad
Attorney, Agent, or Firm—Ostrolenk, Faber, Gerb & Soffen

[57] ABSTRACT

Compounds of formula I $$\underset{Ar-C-COOR^1}{\overset{CHOR^2}{\|}} \qquad (I)$$

in which Ar is aryl and $R^1$ and $R^2$ are alkyl, are obtained by a process in which a compound of formula II $$\underset{Ar-C-COOR^1}{\overset{CHZ}{\|}} \qquad (II)$$

where Z is a disubstituted amino group, a) is reacted with an alcohol, $R^2OH$, preferably under acidic conditions, to give a compound of formula III $$\underset{Ar-CH-COOR^1}{\overset{CH(OR^2)_2}{|}} \qquad (III)$$

which is then dealkanolated, or b) is hydrolysed under acid conditions, to give a compound of formula IV $$\underset{Ar-C-COOR^1}{\overset{CHOH}{\|}} \qquad (IV)$$

which then alkylated. The compounds of formula I have fungicidal activity, as do many of the compounds of formula II, III and IV.

8 Claims, No Drawings

PREPARATION OF PROPENOIC ACID DERIVATIVES

FIELD OF THE INVENTION

This invention relates to a new process for the preparation of certain propenoic acid derivatives.

PRIOR ART

Alkyl 2-aryl-3-alkoxy-2-propenoate derivatives have been disclosed as having pesticidal activity. Compounds of this type are disclosed for example in EPs 178826, 203606, 203608, 206523, 229974, 226917, 242070, 242081, 243012, 243014, 251082, 256667, 260794, 260832, 267734, 270252, 273572, 274825, 278595, 291196, 299694, 307101, 307103, 310954, 312221, 312243, 329011 and 336211. Numerous processes and intermediates for their preparation have been disclosed in these and other publications. In EP 310954 for example certain 3-hydroxy intermediates are disclosed and in GB 2202843, certain 3,3-dimethoxy intermediates are diclosed.

DESCRIPTION OF THE INVENTION

We have now found an improved process for the manufacture of alkyl 2-aryl-3-alkoxy-2-propenoate derivatives. Many intermediates are also novel.

Thus according to one aspect of the invention there is provided a process for the preparation of a compound of formula I

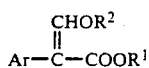 (I)

in which Ar is aryl and $R^1$ and $R^2$ are alkyl, in which a compound of formula II

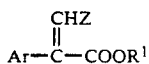 (II)

where Z is a disubstituted amino group, a) is reacted with an alcohol, $R^2OH$, preferably under acidic conditions, to give a compound of formula III

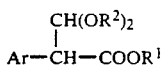 (III)

which is then dealkanolated, or b) is hydrolysed under acid conditions, to give a compound of formula IV

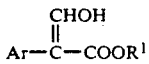 (IV)

which is then alkylated.

The compound of formula II can be obtained by reacting a compound of formula V

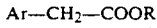 (V)

with a formamide acetal. The particular formamide acetal depends partially on the desired nature of the group Z, but is generally a dialkylformamide dialkylacetal, preferably, dimethylformamide dimethylacetal. This reaction is generally carried out at a temperature between 100° and 180° C., suitably at reflux. If necessary a solvent, e.g. toluene, may be used. A catalyst such as pyridinium tosylate may be present.

The compounds of formula V are either known or can be obtained in known manner.

Z is preferably dialkylamino, especially a dimethylamino group, but the term could also include ring closed amino groups such as morpholino or piperidino and amino substituted by groups such as substituted alkyl, alkenyl, alkynyl, cycloalkyl or aryl.

The reaction with the alcohol in step a) is generally carried out in the presence of a mineral acid, such as hydrochloric or sulphuric acid, at a temperature of e.g. 25° to 150° C., and suitably at reflux.

The dealkanolation reaction in step a) is generally carried out using an alkali metal hydrogen sulphate or an intimate mixture of sulphuric acid and an alkali metal sulphate.

The hydrolysis reaction in step b) is generally carried out in the presence of an acidic ion-exchange resin. Examples of such resins are those composed of nuclear sulphonic acid exchange groups attached to a styrenedivinylbenzene copolymer. The proportion of crosslinking is preferably within the range 2 to 16%. Such resins are sold under various trade names, e.g. Amberlite IR-116 to Amberlite IR-124 or the Dowex-50W series. Macroreticular (macroporous) resins of this type are particularly suitable and are sold under various trade names, e.g. Dowex MSC-1 or Amberlyst 15. It is desirable that this reaction is carried out at moderate temperatures, e.g. 0° to 50° C., and suitably at room temperature.

The alkylation in step b) is suitably carried out in conventional manner, e.g. using an alkyl halide or sulphate, preferably under basic conditions, e.g. in the presence of a metal (especially sodium) hydride.

Since it is generally desired that the compound of formula I is obtained in the E-form, the product is generally heated under acidic conditions to convert any Z-isomer into E-isomer.

The compounds of formula I obtained by the process of the invention are disclosed as having pesticidal and especially fungicidal activity in for example the patents listed in the prior art Ar is preferably an optionally substituted phenyl group or a heteroaryl group and is preferably a) a phenyl group of formula

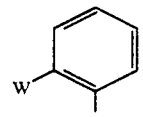

in which W is $R-(CH_2)_m-X_p-(CH_2)_n-$, wherein n is 0 or 1, m is 0 to 18, p is 0 or 1, X is S, O, SO, $SO_2$ or $NR^4$, where $R^4$ is hydrogen, alkyl or acyl, R is aryl, heterocyclyl, heterocyclyl(thio)carbonyl, alkyl, alkenyl, alkynyl and N-substituted iminomethyl, heterocyclylidenemethyl, all of which groups are optionally substituted, b) an optionally substituted heteroaryl group, on which may also be fused an optionally substituted carbocyclic or heterocyclic ring, or c) an optionally substituted phenyl group, on which is fused an optionally substituted carbocyclic or heterocyclic ring.

Many compounds of formula II, III and IV are novel and especially those in which Ar is phenyl, substituted in the ortho position by the group R—CH$_2$—S—, where R is optionally substituted phenyl. Many of them have pesticidal activity and especially fungicidal activity. Certain compounds of formula I are novel.

Fungicidal activity is generally seen against fungal diseases of plants, e.g. mildews and particularly cereal powdery mildew (*Erysiphe graminis*), vine downy mildew (*Plasmopara viticola*), rice blast (*Pyricularia oryzae*), rice sheath blight (*Pellicularia sasakii*), grey mould (*Botrytis cinerea*), potato blight (*Phytophthora infestans*) and apple scab (*Venturia inaequalis*)

When Ar is heteroaryl the hetero atom(s) is preferably nitrogen, but the ring may also comprise other additional or alternative atoms, such as oxygen or sulphur. The Ar ring is preferably substituted in the position ortho to its attachment to the propenoate moiety. Preferred Ar groups are disclosed in our EP 299694.

Of the groups covered by the term R: Alkyl groups are preferably of 1 to 4 carbon atoms, especially methyl or ethyl. Alkenyl and alkynyl groups are generally of three to six carbon atoms. Substituents, when present on any alkyl, alkenyl or alkynyl group, include halogen, alkoxy (e.g. of 1 to 4 carbon atoms), haloalkoxy (e.g. difluoromethoxy) hydroxy, alkylthio, nitro, optionally substituted amino, carboxy, alkoxycarbonyl, cyano, acyloxy and aryl. Aryl groups are usually phenyl, optionally substituted, e.g. by halogen, optionally substituted alkyl or alkoxy, aryl, aryloxy, acyl, nitro, amino, COOH, COOR$^2$, CN, CONR$^2$R$^2$ or S(O)$_n$R$^2$, where R$^2$ and n are as previously defined. The terms heteroaryl and heterocyclyl include groups such as thienyl, furyl, pyridyl, pyrimidinyl, pyrazolyl, thiazolyl, thiazolinyl, thiazolone, oxazolyl, benzimidazolyl, tetrazolyl, benzoxazolyl, thiadiazolyl, dioxolanyl, imidazopyridinyl, 1,3-benzoxazinyl, 1,3-benzothiazinyl, oxazolopyridinyl, triazolyl, triazinyl, imidazolyl, morpholino, benzofuranyl, pyrazolinyl, quinolinyl, quinazolinyl, dihydroquinazolinyl or benzothiazolyl, which themselves may be substituted, e.g. as for phenyl. The term "acyl" includes the residue formed by removal of a hydroxy group from a sulphonic or a phosphorus containing acid as well as from a carboxylic acid. Acyl groups are preferably alkanoyl e.g. of 1 to 4 carbon atoms. Amino groups may be substituted, e.g. by one or two alkyl groups or two substituents can form a ring, e.g. to form a morpholino or piperidino ring. Iminomethyl groups can be substituted both on the nitrogen and carbon. Examples of substituents on the nitrogen include aryl and alkyl. Examples of substituents on the carbon include aryl, alkyl, alkylthio, alkoxy and cyano.

The process of the invention is particularly applicable to the preparation of compounds where Ar is phenyl, substituted in the ortho position by the group R—CH$_2$—X—, where X is oxygen or sulphur and R is optionally substituted phenyl, especially where the substituents on the phenyl are electron withdrawing groups.

The invention is illustrated in the following Examples. Structures of isolated novel compounds were confirmed by elemental and/or other appropriate analyses. Temperatures are in °C.

EXAMPLE 1

A mixture of methyl [2-(2,5-difluorobenzylthio)phenyl]acetate, (15.6 g), dimethylformamide dimethylacetal (23 ml) and pyridinium tosylate (0.2 g) was heated on an oil bath at 140° with distillation of methanol for 4 hours. Excess dimethylformamide dimethylacetal was evaporated under reduced pressure and the residue purified by silica gel column chromatography to give an oil which was recrystallised from diisopropyl ether to give methyl 3-dimethylamino-2-[2-(2,5-difluorobenzylthio)phenyl]prop-2-enoate, mp 97.5°–99° (compound 1A). A mixture of this product (7.26 g), dissolved in acetone (500 ml) and water (15 ml), and Amberlyst 15 (an acidic ion-exchange resin) was stirred at room temperature for 24 hours. The mixture was filtered and the filtrate evaporated, extracted with ether and the extract worked up to give methyl 3-hydroxy-2-[2-(2,5-difluorobenzylthio) phenyl]prop-2-enoate, as a yellow oil, (compound 1B). This (5.3 g) was dissolved in tetrahydrofuran (70 ml) and sodium hydride (0.495 g of 80% dispersion in oil) was added and the mixture stirred for 30 minutes at room temperature. Methyl iodide (2.34 g) was added and the mixture stirred at room temperature overnight and then heated under reflux for 4 hours. Solvent was evaporated and the resulting oil was partitioned between ethyl acetate/ether and water and the organic phase dried and evaporated. The resulting oil was applied to a silica gel chromatography column and eluted with hexane/ethyl acetate to give crude methyl 3-methoxy-2-[2-(2,5-difluorobenzylthio) phenyl]prop-2-enoate, one fraction as the Z-isomer and another fraction as E-isomer. The Z-isomer (2.6 g) was dissolved in toluene (70 ml) and two drops of concentrated sulphuric acid added. The mixture was heated under reflux for two hours, whereby the Z-isomer was converted to the E-isomer. The mixture was washed with water, dried and evaporated and the resulting oil combined with the previously obtained E-isomer. The combined fractions were further purified by column chromatography to give pure methyl (E)-3-methoxy-2-[2-(2,5-difluorobenzylthio) phenyl]prop-2-enoate, as a light brown oil. (Compound 1C).

The starting material was prepared as follows:

A mixture of benzo[b]thiophen-2(3H)-one (11.2 g) aqueous sodium hydroxide (5.58 g in 100 ml water) and tetrahydrofuran (10 ml) was heated under reflux for two hours. A solution of 2,5-difluorobenzyl bromide (15.5 g) in tetrahydrofuran (10 ml) was added and the mixture refluxed for a further 2 hours and allowed to cool. The aqueous layer was clarified by ether extraction and then acidified with concentrated hydrochloric acid. The precipitate was collected, washed with water and dried. The solid was recrystallised from dipropyl ether/hexane to give [2-(2,5-difluorobenzylthio)phenyl]acetic acid, mp 106.5°–107.5°. A solution of this product (14.4 g) in methanol (150 ml) containing concentrated sulphuric acid (0.5 ml) was heated under reflux for 4 hours, cooled and evaporated. The residue was dissolved in ethyl acetate/ether and washed with water and aqueous sodium bicarbonate, dried and evaporated to give methyl [2-(2,5-difluorobenzylthio)phenyl]acetate, as a light brown oil.

In a similar manner there was obtained:

a)

methyl [2-(2,3,4,5,6-pentafluorobenzylthio)phenyl]acetate, which was converted to:

methyl 3-dimethylamino-2-[2-(2,3,4,5,6-pentafluorobenzylthio)phenyl]prop-2-enoate, oil (compound 2A), which in turn was converted to:

methyl 3-hydroxy-2-[2-(2,3,4,5,6-pentafluorobenzylthio)phenyl]prop-2-enoate, oil, (compound 2B), which in turn was converted to:

methyl (E)-3-methoxy-2-[2-(2,3,4,5,6-pentafluorobenzylthio)phenyl]prop-2-enoate, oil, (compound 2C).

b) methyl [2-(2,5-dichlorobenzylthio)phenyl]acetate, which was converted to:

methyl 3-dimethylamino-2-[2-(2,5-dichlorobenzylthio)phenyl]prop-2-enoate, oil (compound 3A), which in turn was converted to:

methyl 3-hydroxy-2-[2-(2,5-dichlorobenzylthio)phenyl]prop-2-enoate, oil, (compound 3B), which in turn was converted to:

methyl (E)-3-methoxy-2-[2-(2,5-dichlorobenzylthio)phenyl]prop-2-enoate, $n_D^{20}$ 1.4278, (compound 3C).

c) methyl [2-(2,5-dibromobenzylthio)phenyl]acetate, which was converted to:

methyl 3-dimethylamino-2-[2-(2,5-dibromobenzylthio)phenyl]prop-2-enoate, oil (compound 4A), which in turn was converted to:

methyl 3-hydroxy-2-[2-(2,5-dibromobenzylthio)phenyl]prop-2-enoate, oil, (compound 4B), which in turn was converted to:

methyl (E)-3-methoxy-2-[2-(2,5-dibromobenzylthio)phenyl]prop-2-enoate, mp 103°, (compound 4C).

d) methyl {2-[2,5-bis(trifluoromethyl)benzylthio]phenyl}acetate, which was converted to:

methyl 3-dimethylamino-2-{2-[2,5-bis(trifluoromethyl)benzylthio]phenyl}prop-2-enoate, mp 126°–7° (compound 5A), which in turn was converted to:

methyl 3-hydroxy-2-{2-[2,5-bis(trifluoromethyl)benzylthio]phenyl}prop-2-enoate, oil, (compound 5B), which in turn was converted to:

methyl (E)-3-methoxy-2-{2-[2,5-bis(trifluoromethyl)benzylthio]phenyl}prop-2-enoate, mp 67°–8°, (compound 5C).

e) methyl [2-(2,3,5,6-tetrafluorobenzylthio)phenyl]acetate, which was converted to:

methyl 3-dimethylamino-2-[2-(2,3,5,6-tetrafluorobenzylthio)phenyl]prop-2-enoate, mp 95°–6°, (compound 6A), which in turn was converted to:

methyl 3-hydroxy-2-[2-(2,3,5,6-tetrafluorobenzylthio)phenyl]prop-2-enoate, oil, (compound 6B), which in turn was converted to:

methyl (E)-3-methoxy-2-[2-(2,3,5,6-tetrafluorobenzylthio)phenyl]prop-2-enoate, mp 106°–7°, (compound 6C).

f) methyl {2-[(2-methylthiazol-4-yl)methylthio]phenyl}acetate, which was converted to:

methyl 3-dimethylamino-2-{2-[(2-methylthiazol-4-yl)methylthio]phenyl}prop-2-enoate, oil, (compound 7A), which in turn was converted to:

methyl 3-hydroxy-2-{2-[(2-methylthiazol-4-yl)methylthio]phenyl}prop-2-enoate, oil, (compound 7B), which in turn was converted to:

methyl (E)-3-methoxy-2-2-[(2-methylthiazol-4-yl)methylthio]phenyl]prop-2-enoate, mp 84°–5°, (compound 7C).

g) methyl [2-(benzylthio)phenyl]acetate, which was converted to:

methyl 3-dimethylamino-2-[2-(benzylthio)phenyl]prop-2-enoate, mp 93°–5°, (compound 8A), which in turn was converted to:

methyl 3-hydroxy-2-[2-(benzylthio)phenyl]prop-2-enoate, mp 78°–80°, (compound 8B), which in turn was converted to:

methyl (E)-3-methoxy-2-[2-(benzylthio)phenyl]prop-2-enoate, mp 71°–4°, (compound 8C).

h) methyl [2-(2,6-dichlorobenzylthio)phenyl]acetate, which was converted to:

methyl 3-dimethylamino-2-[2-(2,6-dichlorobenzylthio)phenyl]prop-2-enoate, mp 123°, (compound 9A), which in turn was converted to:

methyl 3-hydroxy-2-[2-(2,6-dichlorobenzylthio)phenyl]prop-2-enoate, mp 84°–6°, (compound 9B), which in turn was converted to:

methyl (E)-3-methoxy-2-[2-(2,6-dichlorobenzylthio)phenyl]prop-2-enoate, mp 134°–5°, (compound 9C).

i) methyl {2-[(2-phenyl-1,3-dioxolan-2-yl)methylthio]phenyl}acetate, which was converted to:

methyl 3-dimethylamino-2-{2-[(2-phenyl-1,3-dioxolan-2-yl)methylthio]phenyl}prop-2-enoate, mp 115°–7°, (compound 10A), which in turn was converted to:

methyl 3-hydroxy-2-[2-[(2-phenyl-1,3-dioxolan-2-yl)methylthio]phenyl}prop-2-enoate, oil, (compound 10B), which in turn was converted to:

methyl (E)-3-methoxy-2-{2-[(2-phenyl-1,3-dioxolan-2-yl))methylthio]phenyl}prop-2-enoate, oil, (compound 10C).

j) methyl [2-(2,6-dimethylbenzylthio)phenyl]acetate, which was converted to:

methyl 3-dimethylamino-2-[2-(2,6-dimethylbenzylthio)phenyl]prop-2-enoate, mp 131°–3° (compound 11A), which in turn was converted to:

methyl 3-hydroxy-2-[2-(2,6-dimethylbenzylthio)phenyl]prop-2-enoate, mp 114°–6°, (compound 11B), which in turn was converted to:

methyl (E)-3-methoxy-2-[2-(2,6-dimethylbenzylthio)phenyl]prop-2-enoate, mp 100°–1°, (compound 11C).

k) methyl [2-(1-methoxycarbonylethylthio)phenyl]acetate, which was converted to:

methyl 3-dimethylamino-2-[2-(1-methoxycarbonylethylthio)phenyl]prop-2-enoate, oil, (compound 12A), which in turn was converted to:

methyl 3-hydroxy-2-[2-(1-methoxycarbonylethylthio)phenyl]prop-2-enoate, oil, (compound 12B), which in turn was converted to:

methyl (E)-3-methoxy-2-[2-(2-methoxycarbonylethylthio)phenyl]prop-2-enoate, oil, $n^D_{20}$ 1.560, (compound 12C).

EXAMPLE 2

Sodium hydride (2.17 g of an 80% dispersion in oil) was washed with dry petroleum ether then suspended in tetrahydrofuran (150 ml). 2-Mercapto-4,4-dimethyl-5-methylene-2-thiazoline (11.5 g) was added to the mixture, which was then stirred at room temperature for 30 minutes. Methyl (α-bromo-o-tolylphenyl)acetate (16.7 g) was added and the mixture stirred overnight, after which time it was evaporated under reduced pressure and partitioned between ether and water. The organic phase was washed with water, dried over magnesium sulphate and evaporated to give an oil which was purified by chromatography (stationary phase: silica, eluent: gradient elution from 2% ether in petrol to 10% ether in petrol) to give methyl [α-(4,4-dimethyl-5-methylene-2-thiazolin-2-ylthio)-o-tolyl]acetate.

This product (5.21 g), dimethylformamide dimethyl acetal (4.8 g) and pyridinium tosylate were heated together in a flask equipped with a Vigreaux column topped by a distillation head. The mixture was heated by an oil bath at 95° for 6 hours, causing the methanol produced by reaction to slowly distil off. The reaction mixture was then cooled, diluted with an aqueous solution of sodium hydrogen carbonate and extracted into ethyl acetate. The extract was washed with water, dried over magnesium sulphate and evaporated to give an oil which was purified by column chromatography (stationary phase: silica, eluent: 4:1 hexane:ethyl acetate) to give methyl 3-dimethylamino-2-[α-(4,4-dimethyl-5-methylene-2-thiazolin-2-ylthio)-o-tolyl]prop-2-enoate. (Compound 13A)

This product (1.0 g), methanol (10 ml) and concentrated sulphuric acid (0.1 ml) were mixed and heated under reflux for 3 hours. The mixture was cooled, evaporated under reduced pressure and partitioned between ether and water. The ether extracts were washed with water, dried over magnesium sulphate and evaporated to an oil which was purified by column chromatography (stationary phase: silica, eluent 9:1 hexane:ethyl acetate) to give methyl 2-[α-(4,4-dimethyl-5-methylene-2-thiazolin-2-ylthio)-o-tolyl]-3,3-dimethoxypropionate, oil. (Compound 13B)

This product (100 mg) and sodium bisulphate were heated on a steam bath in a flask evacuated to 200 mm Hg for 2 hours. The residue was triturated with ether and filtered. The filtrate was evaporated under reduced pressure. The product was recrystallised from ether/petrol to give methyl (E)-2-[α-(4,4-dimethyl-5-methylene-2-thiazolin-2-ylthio)-o-tolyl ]-3-methoxyprop-2-enoate, mp 101°. (compound 13C)

EXAMPLE 3

Using a similar method to that described in Example 2, there was obtained methyl {2-[(5-trifluoromethylbenzothiazol-2-yl)thiomethyl]phenyl}acetate, which was converted to methyl 3-dimethylamino-2-{2-[(5-trifluoromethylbenzothiazol-2-yl)thiomethyl]phenyl} prop-2-enoate, mp 122°-3°, (compound 14A), using a similar method to that described in Example 1. This was converted to methyl 3-hydroxy-2-{2-[(5-trifluoromethylbenzothiazol-2-yl)thiomethyl]phenyl}prop-2-enoate, mp 69°-72°, (compound 14B), which in turn was converted to: methyl (E)-3-methoxy-2-{2-[(5-trifluoromethylbenzothiazol-2-yl)thiomethyl]phenyl} prop-2-enoate, mp 97°-99°, (compound 14C).

In a similar manner there was obtained a) methyl {2-[[(phenylimino)(methylthio)methyl]thiomethyl]phenyl}acetate, which was converted to methyl 3-dimethylamino-2-{2-[[(phenylimino)(methylthio)methyl]thiomethyl]phenyl}prop-2-enoate, oil, (compound 15A), which in turn was converted to methyl 3-hydroxy-2-{2-[[(phenylimino)(methylthio)methyl]-thiomethyl]phenyl]prop-2-enoate, oil, (compound 15B), which in turn was converted to methyl (E)-3-methoxy-2-{2-[[(phenylimino)(methylthio)methyl]thiomethyl]phenyl}prop-2-enoate, gum, (compound 15C)

EXAMPLE 4

In a similar to that described in Example 1, compound 14A was converted to methyl 3-hydroxy-2-[α-(4,4-dimethyl-5-methylene-2-thiazolin-2-ylthio)-o-tolyl-]acrylate, oil, (Compound 13D), which in turn was converted to compound 13C, mp 101°.

EXAMPLE 5

Using a similar method to that described in Example 1, there was obtained methyl [2-(3-methoxybenzylthio)-phenyl]acetate, which was converted to methyl 3-dimethylamino-2-[2-(3-methoxybenzylthio)phenyl]prop-2-enoate, mp 92°-4°, (compound 16A), which in turn was converted to methyl 2-[2-(3-methoxybenzylthio)-phenyl]-3,3-dimethoxypropionate, oil, (compound 16B), which in turn was converted to methyl (E)-3-methoxy-2-[2-(3-methoxybenzylthio)phenyl]prop-2-enoate, mp 87°-9°, (compound 16C).

In a similar manner there was obtained: methyl {2-[(3,5-dimethylisoxazol-4-yl)methylthio]phenyl}acetate, which was converted to methyl 3-dimethylamino-2-{2-[(3,5-dimethylisoxazol-4-yl)methylthio]phenyl}prop-2-enoate, mp 82°-6°, (compound 17A), which in turn was converted to methyl 2-{2-[(3,5-dimethylisoxazol-4-yl)methylthio]phenyl}-3,3-dimethoxypropionate, oil, (compound 17B), which in turn was converted to methyl (E)-3-methoxy-2-{2-[(3,5-dimethylisoxazol-4-yl)methylthio]phenyl}prop-2-enoate, oil, (compound 17C).

EXAMPLE 6

In a similar manner to Example 2:

a) compound 8A was converted to methyl 2-(2-benzylthiophenyl)-3,3-dimethoxypropionate, mp 49°-51°, (compound 8D), which in turn was converted to compound 8C, and b) compound 14A was converted to methyl 2-(5-trifluoromethylbenzothiazol-2-yl)-3,3-dimethoxypropionate, off white solid, (compound 14D), which in turn was converted to compound 14C.

NMR spectral data for enoate esters which do not have a characterising melting point or refractive index Chemical shifts are measured in ppm in tetramethylsilane (TMS). Unless otherwise stated the solvent used was deuteriochloroform. The abbreviations have the following meanings:

| Compound | NMR data (δ relative to TMS) |
|---|---|
| 1C | 3.75(3H, s, OMe), 3.84(3H, s, CO$_2$Me), 4.03(2H, s, CH$_2$), 6.8–7.0(3H, m, ArH), 7.15–7.3(4H, m, ArH), 7.56(1H, s, =CH). |
| 2A | 2.58(6H, s, NMe$_2$), 3.44(3H, s, OMe), 4.21(2H, s, CH$_2$), 7.04–7.42(4H, m, ArH), 7.44(1H, s, =CH) |
| 2B | 3.52(3H, s, OMe), 4.08(2H, s, CH$_2$), 7.0–7.6(4H, m, ArH), 7.7(1H, brs, =CH), 10.78(1H, brs, OH) |
| 2C | 3.72(3H, s, OMe), 3.82(3H, s, CO$_2$Me), 4.02(2H, s, CH$_2$), 7.14–7.45(4H, m, ArH), 7.47(1H, s, =CH). |
| 3A | 2.7(6H, s, NMe$_2$), 3.65(3H, s. OMe), 4.12(2H, q, CH$_2$), 7.0–7.45(7H, m, ArH), 7.6(1H, s, =CH) |
| 3B (enol tautomer) | 3.78(3H, s, OMe), 4.05(2H, s, CH$_2$), 6.93(1H, d, =CH), 7.0–7.6(7H, m, ArH), 11.82(1H, d, OH) (peaks arising from the minor aldehyde tautomer are also seen when a deuteriochloroform solution is used to obtain the spectrum). |
| 4A | 2.68(6H, s, NMe$_2$), 3.65(3H, s, OMe), 4.14(2H, q, CH$_2$), 7.0–7.45(7H, m, Ar), 7.61(1H, s, =CH) |
| 4B (enol tautomer) | 3.75(3H, s, Me), 4.05(2H, s, CH$_2$), 6.93(1H, d, CH), 7.05–7.6(7H, m, Ar), 11.81(1H, d, OH) |

| Compound | NMR data (δ relative to TMS) |
|---|---|
| | (peaks arising from the minor aldehyde tautomer are also seen when a deuteriochloroform solution is used to obtain the spectrum). |
| 6B | 3.74(3H, s, OMe), 4.02(2H, s, CH$_2$), 6.97(1H, m, ArH), 7.00(1H, d, =CH), 7.16(1H, m, ArH), 7.27(2H, m, ArH) 7.33(1H, m, ArH), 11.81(1H, d, OH) |
| 7A | 2.68(3H, s, HetMe), 2.70(6H, s, NMe$_2$) 3.64(3H, s, OMe), 4.21(2H, s, CH$_2$), 6.98(1H, s, HetH), 7.0–7.2(4H, m, ArH), 7.60(1H, s, =CH) |
| 7C | 2.73(3H, s, HetMe, 3.78(3H, s, OMe), 4.17(2H, s, CH$_2$), 6.80(1H, s, HetH), 7.06(1H, s, =CH), 7.1–7.4(4H, m, ArH), 11.86(1H, d, OH) |
| 10C | 3.35(2H, s, CH$_2$), 3.67(3H, s, OMe), 3.67(3H, s, COOMe), 3.82(2H, m, O—CH$_2$—CH$_2$—O), 4.10(2H, m, O—CH$_2$—CH$_2$—O) 7.1–7.6(10H, m, 9×ArH8<– =CH) |
| 12A | 1.50+1.48(3H, 2×d, CH$_3$CH), 2.67(6H, brs, NMe$_2$), 3.60+3.61(3H, 2×s, COOMe), 3.69+3.70(3H, 2×s, COOMe), 3.84+3.94(1H, 2×q, CHMe), 7.1–7.3(4H, m, ArH), 7.48+7.49(1H, 2×s, =CH) |
| 12B | 1.43(3H, d, Me), 3.64(3H, s, COOMe), 3.74(3H, s, COOMe), 3.70(1H, obscured m, CHMe), 7.13(1H, d, =CH), 7.18(1H, m, ArH), 7.30(2H, m, ArH), 7.52(2H, m, ArH), 11.87(1H, d, OH) | br broad
d doublet
m multiplet
q quartet
s singlet
t triplet

Compounds 1–17A, 1–17B, 1–4C, 8D, 13D and 14D are novel compounds and form one aspect of the invention.

In a similar to manner to Example 1, methyl (2-methylphenyl)acetate was converted to methyl (E)-3-dimethylamino-2-(2-methylphenyl)prop-2-enoate, bp 125°–7°/0.1 mm, which on cooling gave a crystalline solid, mp 48°–49°. This was then hydrolysed in a similar manner to Example 1, but using Amberlite IR 120 resin instead of Amberlyst 15, to give methyl (Z)-3-hydroxy-2-(2-methylphenyl)prop-2-enoate, obtained as an oil and which had the following nmr spectral data: 2.15(3H,s,Me), 3.67(3H,s,CO$_2$Me), 7.0–7.4(5H,m,ArH and =CH), 11.8(1H,d,OH)

TEST EXAMPLE A

Compounds are assessed for activity against one or more of the following:
*Botrytis cinerea:* grey mould of tomato (BC)
*Plasmopara viticola:* vine downy mildew (PV)
*Pyricularia oryzae:* rice blast (PO)
*Venturia inaequalis:* apple scab (VI)

Aqueous solutions or dispersions of the compounds at the desired concentration, including a wetting agent, were applied by spray or by drenching the stem base of the test plants. These plants were then inoculated with appropriate test pathogens and kept under controlled environment conditions suitable for maintaining plant growth and development of the disease. After an appropriate time, the degree of infection of the leaf surface was visually estimated. Compounds were considered active if they gave greater than 50% control of the disease at a concentration of 500 ppm (w/v) or less. Compounds 1A, 1B, 1C, 8B, 11B, 13A, 13B, 13D, 14A, 14B, 15A and 15B were active against PV; compounds 1C, 8B, 11B, 13A, 13D, 14A, 14B and 15A were active against PO; compounds 1A, IB, 6A, 9B, 13B and 16B were active against VI and compounds 9A and 17A were active against BC.

We claim:

1. A process for the preparation of a compound of

which Ar is aryl and R$^1$ and R$^2$ are alkyl, in which a compound of formula II

where Z is a disubstituted amino group,
a) is reacted with an alcohol, R$^2$OH, preferably under acidic conditions, to give a compound of formula III

which is then dealkanolated, or
b) is hydrolysed under acid conditions, to give a compound of formula IV

which is then alkylated.

2. A process according to claim 1, in which R$^1$ and R$^2$ are methyl.

3. A process according to claim 1, in which the compound of formula II is obtained by reacting a compound of formula V

with a formamide acetal.

4. A process according to claim 3 in which the formamide acetal is a dialkylformamide dialkylacetal.

5. A process according to claim 4 in which the dialkylformamide dialkylacetal is dimethylformamide dimethylacetal.

6. A process according to claim 1 in which the hydrolysis in step b) is carried out in the presence of an acidic ion-exchange resin.

7. A process according to claim 1 in which the hydrolysis in step b) is carried out at temperature of 0° to 50° C.

8. A process according to claim 1 in which Ar is
a) a phenyl group of formula

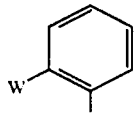

in which

W is $R-(CH_2)_m-X_p-(CH_2)_n-$, wherein n is 0 or 1, m is 0 to 18, p is 0 or 1, X is S, O, SO, $SO_2$ or $NR^4$, where $R^4$ is hydrogen, alkyl or acyl, and R is aryl, heterocyclyl, heterocyclyl(thio)carbonyl, alkyl, alkenyl, alkynyl and N-substituted iminomethyl, heterocyclylidenemethyl, all of which groups are optionally substituted, b) an optionally substituted heteroaryl group, on which may also be fused an optionally substituted carbocyclic or heterocyclic ring, or c) an optionally substituted phenyl group, on which is fused an optionally substituted carbocyclic or heterocyclic ring.

* * * * *